(12) United States Patent
Farries et al.

(10) Patent No.: US 9,603,912 B2
(45) Date of Patent: Mar. 28, 2017

(54) CANCER THERAPY

(75) Inventors: Timothy Farries, London (GB); David Eckland, London (GB)

(73) Assignee: Glrotherapy Limited, Chinnor (GB)

( * ) Notice: Subject to any disclaimer, the term of this patent is extended or adjusted under 35 U.S.C. 154(b) by 1080 days.

(21) Appl. No.: 13/392,570

(22) PCT Filed: Sep. 23, 2010

(86) PCT No.: PCT/GB2010/051595
§ 371 (c)(1),
(2), (4) Date: Mar. 12, 2012

(87) PCT Pub. No.: WO2011/063487
PCT Pub. Date: Mar. 31, 2011

(65) Prior Publication Data
US 2012/0164172 A1    Jun. 28, 2012

(30) Foreign Application Priority Data
Sep. 28, 2009 (GB) .................................. 09169970

(51) Int. Cl.
*A61K 39/00* (2006.01)
*A61K 48/00* (2006.01)
*G01N 33/53* (2006.01)
*G01N 33/50* (2006.01)
*G01N 33/68* (2006.01)
*A61K 38/45* (2006.01)

(52) U.S. Cl.
CPC .......... *A61K 39/0011* (2013.01); *A61K 38/45* (2013.01); *A61K 48/005* (2013.01); *C12Y 207/01021* (2013.01); *G01N 33/505* (2013.01); *G01N 33/6854* (2013.01); *A61K 2039/53* (2013.01); *A61K 2039/555* (2013.01); *C12N 2799/022* (2013.01); *G01N 2800/52* (2013.01)

(58) Field of Classification Search
CPC ............. A61K 39/0011; G01N 33/505; C12Y 207/010211
See application file for complete search history.

(56) References Cited

U.S. PATENT DOCUMENTS 5,631,236 A    5/1997  Chen et al.
6,579,855 B1 *  6/2003  Yla-Herttuala et al. .... 514/44 R

OTHER PUBLICATIONS

Bramson et al. (1997) Pre-existing immunity to adenovirus does not prevent tumor regression following intratumoral administration of a vector expressing IL-12 but inhibits virus dissemination. Gene Therapy, 4:1069-1076.*
Ulasov et al. (2009) Combination of adenoviral virotherapy and temozolomide chemotherapy eradicates malignant glioma through autophagic and apoptotic cell death in vivo. British Journal of Cancer, 100:1154-1164.*
Pulkkanen et al. (2005) Gene Therapy for Malignant Glioma: Current Clinical Status. Molecular Therapy, 12(4):585-598.*
King et al. (2008) High-Capacity Adenovirus Vector-Mediated Anti-Glioma Gene Therapy in the Presence of Systemic Antiadenovirus Immunity. Journal of Virology, 82(9):4680-4684.*
Perez-Cruet, M.J., et al., "Adenovirus Mediated Gene Therapy of Experimental Gliomas," Journal of Neuroscience, (1994) 39(4) 506-511.
Chen, Shu-Hsia et al., "Gene Therapy for Brain Tumours: Regression of Experimental Gliomas by Adenovirus-mediated Gene Transfer in vivo," Proc. Natl. Acad. Sci., (1994) 91(8) 3054-3057.
Maron, A., et al., "Gene Therapy of Rat C6 Glioma Using Adenovirus-mediated Transfer of the Herpes Symplex Virus Thimidine Kinase Gene: Long-term Follow Up by Magnetic Resonance Imaging," Gene Therapy (1996) 3, 315-322.
Barcia, C. et al., "One-year Expression From High-capacity Adenoviral Vectors in the Brains of Animals with Preexisting Anti-adenoviral Immunity: Clinical Implications," Molecular Therapy (2007) 15(12) 2154-2163.
Brouwer, E. et al., "Human Adenovirus Type 35 Vector for Gene Therapy of Brain Cancer: Improved Transduction and Bypass of Pre-existing Anti-vector Immunity in Cancer Patients," Cancer Gene Therapy (2007) 14, 211-219.
King, G.D., et al., "High-Capacity Adenovirus Vector-Mediated Anti-Glioma Gene Therapy in the Presence of Systemic Antiadenovirus Immunity," J. Virology (2008) 82 (9) 4680-4684.
King, G.D., et al., "FIt3L and TK Gene Therapy Eradicate Multifocal Glioma in a Syngeneic Glioblastoma Model," Neuro-Oncology (2007) 10, 19-31.
Okada, H., et al., "Immunotherapeutic Approaches for Glioma," Crit Rev Immunol (2009) 29(1), 1-42.
Curtin, J.F., et al., "HMGB1 Mediates Endogenous TLR2 Activation and Brain Tumor Regression," PLoS Medicine (2009) 6(1) 83-104.

* cited by examiner

*Primary Examiner* — Neil P Hammell
(74) *Attorney, Agent, or Firm* — Pharmaceutical Patent Attorneys, LLC

(57) ABSTRACT

An agent that stimulates antiviral immunity may be used, for the treatment of cancer. A product comprising an immunostimulant and a vector comprising a transgene that promotes death of neoplastic cells, may also be used for simultaneous, sequential or separate administration in the treatment of cancer.

28 Claims, No Drawings

CANCER THERAPY

This application asserts priority from and is a National Stage of PCT Application Ser. No. PCT/GB2010/051595 filed 23 Sept. 2010, which asserts priority from Great Britain provisional patent filing Ser. No. 09/169970 filed 28 Sept. 2009, the contents of which are here incorporated by reference.

FIELD OF THE INVENTION

The present invention relates to gene therapies for cancer.

BACKGROUND OF THE INVENTION

Cancers are a major cause of mortality. High grade gliomas are particularly devastating malignant tumours, for which there is currently no effective cure and for which the outcome is normally fatal. Certain treatments can prolong survival, but they do not cure the cancer.

Malignant glioma is a cancerous tumour that is confined to the brain and only rarely spreads further. The current standard therapy involves surgically removing the solid tumour mass and initiating radiotherapy and/or chemotherapy. Even when the solid tumour mass is being removed, precancerous or isolated cancerous cells can exist in the brain. In the majority of these patients, a new tumour grows and a repeat operation is frequently required. Currently most available cancer medicines are generally very toxic and many do not readily reach the brain tumour. They often cause severe side effects that can reduce the patient's quality of life significantly.

EP1135513 relates to an adenovirus-based gene therapy. The therapy involves the use of adenovirus having a functional thymidine kinase gene, for the treatment of a brain tumour cavity resulting from tumour resection. Following standard surgery to remove the solid tumour mass, the adenovirus is injected through the wall of the cavity left behind by the surgical removal of the solid tumour, in to the surrounding healthy brain tissue. This causes the healthy cells in the wall of the cavity to express Herpes simplex virus thymidine kinase (HSV-tk). The drug ganciclovir is then given to the patient. HSV-tk and ganciclovir react together to produce a substance which destroys cells when they try to divide. This prevents another tumour growing around the site of the removal of the original tumour.

The therapy "Cerepro", developed by the Applicant, is based on the above principal. It has been shown in clinical trials to have therapeutic benefits for patients with high grade glioma.

Previous evidence and current general expectation is that pre-existing antibodies that have the ability to neutralise adenovirus infectivity, will inhibit the therapeutic activity of medicinal adenoviral gene therapy vectors. This is because it is believed that they will inhibit their ability to infect tissue, and therefore their ability to effect expression of the transgene. Evidence for this may be found in King et al, 2008, which describes treatment with an Ad-HSV-tk vector and ganciclovir, in a rat glioma model. It was found that the treatment induced tumour regression and prolonged survival, but was ineffective in rats that were pre-immunised with the vector. The authors proposed that less immunogenic "gutless" adenoviral vectors would be required for clinical efficacy in patients that had pre-existing immunity to the adenovirus.

Further, in Barcia et al., 2007, it was found that prolonged expression of a marker gene from an adenoviral vector injected into the mouse brain was prevented by pre-immunising the mouse with adenovirus. Prolonged expression could be achieved in pre-immunised mice if a less immunogenic "gutless" adenoviral vector was used. Additionally, in Brouwer E et al., 2007, the authors proposed that adenoviral vectors based on Ad35 would be clinically preferable to Ad5-based vectors for treatment of malignant glioma because of the inhibitory effect of pre-existing immunity to the Ad5 vectors.

Okada et al 2009, propose using cytokines to maximise specific anti-tumour immunity when using an Ad-HSV-tk vector with ganciclovir. When the group tested various immunostimulatory therapies in a rat model of glioma, only fms-like tyrosine kinase ligand (Flt3L) was effective delivered in combination with Ad-HSV-tk, whereas CD40L and IL-12 were not effective. The immunosuppressor cyclosporine A inhibited the efficacy. It is important to realise that the experiments were carried out in a rat model, which is not an accurate indicator of therapeutic effect in humans. Also, the treatment is based on using tumour antigens.

SUMMARY OF THE INVENTION

The present invention is based on a study, which shows that locally administered antigens in combination with a pre-existing immunoresponsiveness to those antigens, enhances the efficacy of an adenoviral-based gene therapy treatment for glioma.

Therefore, according to a first aspect the present invention is an agent that stimulates antiviral immunity, for the treatment of cancer.

According to a second aspect, the present invention is a product comprising an immunostimulant and a vector comprising a transgene that promotes death of neoplastic cells, for simultaneous, sequential or separate administration in the treatment of cancer.

According to a third aspect, the present invention is a method of selecting patients for treatment with a product as defined above, comprising determining ex vivo the level of immunity against the vector, in a sample taken from a patient, and selecting the patient for treatment if the level of immunity is above a pre-determined level.

According to a fourth aspect, the present invention is a method of predicting the efficacy of a product as defined above, comprising determining ex vivo the level of immunity against the vector, in a sample taken from a patient, and selecting the patient for treatment if the level of immunity is above a pre-determined level.

According to a fifth aspect, the present invention is a method of treating cancer, comprising administering a course of a product as defined above, followed by administering a second course of the product after a period of time sufficient for the patient to generate a specified level of immunity to the vector.

DESCRIPTION OF THE PREFERRED EMBODIMENTS

Without wishing to be bound by theory, it is proposed that when an immunostimulant is administered with a viral vector-based gene therapy for cancer, reactions between the components create a local environment that is conductive to recruitment of additional anti-neoplastic cell processors, such as the generation of immune responses directed against the neoplastic cells. Therefore, in contrast to the findings of most the prior art cited above, it has been found in the present invention that pre-existing immunoresponsiveness to adenoviral vectors will enhance its sufficiency for the treatment of cancer.

The skilled person will know how to carry out the invention described in the claims. The gene therapy "Cerepro" is in the public domain and suitable dosages, methods of administration etc are known. Information relevant to the present invention is also disclosed in EP1135513, which is incorporated herein by reference.

Suitable dosages and methods of administration for the immunostimulant will be readily apparent to the skilled person.

Preferably, the vector is a viral vector. More preferably, the viral vector is an adenovirus.

In a preferred embodiment, stimulation of the immune system is used to increase the immunoresponsiveness of the patient that is to be administered vector antigens to enhance the therapeutic efficacy of the gene therapy adenoviral vector. This immunostimulation may be achieved by either non-specific activation of immune reactions or by stimulation specifically relating to the therapy by the immunogenes (or antigens) of the gene therapy vector, or the tumour.

In a further preferred embodiment, an antigenic component to which the patient has pre-existing immunoresponsiveness, is co-administered with an anti-tumour agent such that the consequent immune reactions enhance the efficacy of the anti-tumour therapy. In the case of a viral vector, the co-administered antigens may be antigenic components of the viral particles themselves, i.e. they may be integral with the vector. Alternatively, they may be provided separately.

In a further preferred embodiment, the degree of anti-tumour efficacy of a therapeutic agent may be predicted by assessment of the state of immunoresponsiveness of the patients to the antigens in the therapeutic agent, prior to treatment. This criterion might be useful for the management of the patient, including for the selection of the most appropriate course of medication.

The immunoresponsiveness of the patient may be determined by determining ex vivo the amount of antibodies against the vector. However, other methods of measuring immunoresponsiveness against the vector will be known to those skilled in the art and are included within the scope of the invention. For example, immunity could be determined by measuring the level of T-cells in the patient, or by taking a life-history of exposure to the vector.

The results of the study on which the invention is based (shown below), show that the efficacy of an Ad-HSV-tk vector in the treatment of high grade glioma, is enhanced in a state of immunoresponsiveness to the adenoviral vector, as signified by the presence of neutralising anti-adenoviral antibodies.

The study uses an Ad-HSV-tk vector. However, other gene therapy vectors may be suitable for use in the invention. Also, the present invention is not limited to the treatment of high grade glioma; it is potentially applicable to all cancers.

Preferably, the agent that stimulates antiviral immunity is selected from:
Adenoviral particles (or derived antigen preparations);
Other viral particles (or derived antigen preparations);
Other specific immunogens stimulating an immune response against a specific target antigen.

Immunogens may be administered in combination with an adjuvant or other form of general immunostimulation, as described below.

Preferably, an immunostimulant suitable for use of the invention is a general immunostimulant, which may be selected from preparations including microbial components, for example:
Bacterial lipopolysaccaharides;
BCG (Bacillus Calmette-Guérin);
Freund's complete adjuvant;
Ribi Adjuvant System (RAS);
Preparations that stimulate Toll-like receptors; E.g. CpG DNA
Thymomimetic agents such as:
thymosin α1;
levamisole;
methyl inosine monophosphate (MIMP);
Antibodies that bind to and stimulate immune responses or inhibit suppressor immune responses, e.g. "superagonistic antibodies" (e.g. Tegenero TGN1412);
Virosomes;
Any other known adjuvant, such as:
Freund's incomplete adjuvant;
Titermax;
Syntex Adjuvant Formulation;
ALUM—aluminum hydroxide;
Elvax 40W;
Montanide;
AdjuPrime;
Gerbu adjuvant;
Modifications to the immunogens to provide costimulation of immune cells to enhance the immune response to those immunogens, for example:
Coating the immunogen with complement C3d fragment;
Protein binding substrates such as "SuperCarrier", or Nitrocellulose-absorbed protein;
Coprecipitation with L-Tyrosine;
Immune-stimulating complexes (ISCOMS);
Cytokines—administered as protein or an agent that causes their expression or activation;

In a preferred embodiment, the immunostimulant is an agent that reduces immunosuppression. Examples include:
Reduction in steroids such as glucocorticoids given therapeutically for the period of administration of the cytotoxic mediator;
Cessation, reduction or avoidance of other immunosuppressants such as:
Agents acting on immunophilins, such as Cyclosporine A;
Cytostatice purine analogs;
Methotrexate;
Immunosuppressive antibodies such as OKT3.
For the period of treatment and its effect, cessation, reduction or avoidance of other medicinal agents or treatments that have immunosuppressive activities, e.g.:
Radiation;

The immunostimulation may be administered systemically or locally. Further, the timing should be such to ensure that the immunostimulation is effective for the period during exposure to administered antigens.

The antigens may be one or both of the following:
Part of the therapeutic agent's property. In the case of a gene therapy vector, this includes any of the following:
The vector has the antigenic properties to react with pre-existing immunoresponsiveness;
Antigens expressed by cells infected with the vector, such as a protein expressed from a vector gene product; or
Administered as a separate material (which may be mixed and/or co-administered with the therapeutic agent).

In a preferred embodiment the antigens are derived from a preparation of adenoviral particles or proteins that are administered to patients with pre-existing immunoresponsiveness to adenoviral antigens.

Assessment of the state of immunoresponsiveness of a patient may be achieved from:

Tests for the presence of antibodies or lymphocytes reacting against the antigens to be administered (such as antibodies against the viral vector);

Tests for general immunocompetence, such as tests for other specific antibodies or for lymphocyte numbers or functions;

Review of the patient's history for evidence of prior exposure to the antigens to be administered (e.g. from prior infection or immunisation), general immune insufficiency (e.g. as may be signified by a propensity for infections) or immunosuppressive factors (such as other medications).

Use of knowledge of a patient's state of immunoresponsiveness to the antigens to be administered to predict efficacy of the gene therapy in those patients may be used for:

Determining if the patient should receive antigen-specific or general immunostimulation before treatment with the gene therapy;

Determining if the patient being treated with the gene therapy should discontinue, reduce or avoid treatments with immunosuppressive effects;

Determining if the risk-benefit makes it appropriate to treat the patient with the gene therapy.

The invention is illustrated by the following study:

Study

The clinical Study was entitled "A Controlled, Randomised, Parallel Group, Multicentre Study of the Efficacy and Safety of Herpes simplex Virus-Thymidine Kinase Gene Therapy (Cerepro™), with Subsequent Ganciclovir, for the Treatment of Patients with Operable High-Grade Glioma". This was a Phase III, multicentre, controlled, randomised, parallel group clinical study of the efficacy and safety of *Herpes Simplex* virus-thymidine kinase gene therapy (Cerepro®) with subsequent GCV for the treatment of patients with operable primary glioblastoma. The study was comprised of two treatment groups: an active group and a control group. The active group received standard care plus a one-time treatment with Cerepro® (which occurred after surgical resection of the tumour) followed by a 14-day treatment with GCV. The control group received standard care after surgical resection of the tumour. The primary objective of this study was to determine if Cerepro/Ganciclovir (GCV) is superior to standard care for the treatment of operable primary glioblastoma based on time to death or re-intervention [reintervention is defined as any kind of treatment (including surgery, radiotherapy or chemotherapy) given to prolong survival when a tumour recurs]. Data on all cause mortality (time to death) was also collected. Many patients also received temozolamide and statistical analyses of efficacy have been conducted that included this as a covariate to account for its contribution to the overall efficacy.

Patient serum samples were tested for titres of neutralising anti-adenovirus antibodies at screening and various time-points thereafter. The titre of neutralising Adv-Abs was assessed by incubating serial dilutions of the subject's serum with adenovirus type 5 (replication deficient). The serum/adenovirus mix was then incubated with HEK293 detector cells. The cytopathic effect of any non-neutralised adenovirus was measured using alamar blue (which stains live cells). The neutralising antibody titer is expressed as the reciprocal of the dilution or dilutions (assessed in multiple replicates) which caused a cytopathic effect in 50% of the detector cells.

When the end-point data were analysed with respect to the pre-treatment (baseline) titre of neutralising anti-adenoviral antibodies it was found that the efficacy of Cerepro was more profound in those patients in which there detectable neutralising antibodies at baseline. As shown in the tables below the median survivals and therapeutic hazard ratios for Cerepro are higher (higher hazard ratios indicate greater efficacy) in patients that have pre-existing antibodies (defined as any neutralising antibody activity in the test), than those that don't and the effect is even more pronounced in patients with higher antibody titres (>100). For the standard care group which did not receive Cerepro the presence of pre-existing antibodies conferred no advantage compared to those patients without detectable pre-existing neutralising anti-adenoviral antibodies, showing that in this indication neither the presence of the antibodies, nor the state of immunocompetence that they are indicative of, has such beneficial effect without combination with Ad.HSV-tk.

TABLE 1

Times to reintervention or death (primary end-point), or to all cause mortality (death), for patients in study 904 examining the effect of baseline anti adenoviral antibodies (derived from study data updated as of March 2009).

| | Cerepro | | | Standard Care | | |
|---|---|---|---|---|---|---|
| | No Pre-existing Antibodies n = 61 | Pre-existing Antibodies n = 53 | Pre-existing Antibody titre >100 n = 29 | No Pre-existing Antibodies n = 70 | Pre-existing Antibodies n = 45 | Pre-existing Antibody titre >100 n = 18 |
| Time (days) to re-intervention or death Median (95% CI) | 296 (217, 378) | 352 (293, 430) | 373 (284, 485) | 267 (208, 313) | 250 (189, 386) | 236 (157, 386) |
| Time (days) to death Median (95% CI) | 387 (327, 624) | 550 (376, 642) | 574 (373, 691) | 497 (396, 572) | 490 (376, 576) | 481 (315, 600) |

TABLE 2

Hazard ratios and p values for Cerepro compared with Standard Care in patients with different titres of anti-adenoviral antibodies at baseline.

| Antibody titre (n) | Hazard Ratio for primary endpoint (95% CI) | P-value vs. Standard care | Hazard Ratio for all cause mortality (95% CI) | P-value vs. Standard care |
|---|---|---|---|---|
| 0 (131) | 1.29 (0.86, 1.93) | 0.221 | 1.07 (0.68, 1.66) | 0.778 |
| >0 (98) | 1.55 (0.98, 2.45) | 0.063 | 1.76 (1.07, 2.87) | 0.025 |
| >100 (47) | 2.17 (1.01, 4.64) | 0.047 | 1.89 (0.85, 4.16) | 0.12 |

The p-values are calculated from a Cox model including terms for treatment, temozolomide use, age and Karnofsky Performance Scoreat Day 19 (D19KPS) in the various subgroups.
Temozolomide and D19 KPS are fitted as time dependent covariates (derived from study data updated as of March 2009).

This exemplifies the following aspects of the invention:

Enhanced efficacy of the Ad-HSV-tk anti-tumour treatment when administered to patients with higher immunoresponsiveness to the adenovirus. Administration of an antigenic agent to patient with pre-existing immunity to that agent so that immune reactions enhance the anti-neoplastic efficacy of that agent.

Utility of assessment of the immunoresponsiveness of a patient to the administered antigenic component to predict the efficacy of a gene therapy treatment in that patient.

REFERENCES

Barcia C et al., 2007 Mol Ther. 15:2154-63, "One-year expression from high-capacity adenoviral vectors in the brains of animals with pre-existing anti-adenoviral immunity: clinical implications."
Brouwer E et al, 2007, Cancer Gene Ther. 14:211-9, "Human adenovirus type 35 vector for gene therapy of brain cancer: improved transduction and bypass of pre-existing anti-vector immunity in cancer patients".
King GD et al., 2008, J Virol. 82:4680-4, "High-capacity adenovirus vector-mediated anti-glioma gene therapy in the presence of systemic antiadenovirus immunity."
Okada H et al 2009 Crit Rev Immunol 29, 1-42 Immunotherapeutic Approaches for Glioma.

The invention claimed is:

1. In a method of treating cancer in a human by partial or complete resection of tumor from said human, the improvement comprising:
   a. Determining the level of immunity against a viral vector, and then
   b. Confirming said human has a measurable level of immunity against said vector, and then
   c. Administering to said human said viral vector.

2. The method of claim 1, wherein said administering to said human said viral vector comprises administering to the cavity created by said resection of said tumor.

3. The method of claim 1, wherein said viral vector comprises adenovirus.

4. The method of claim 1, wherein said viral vector comprises a transgene.

5. The method of claim 4, wherein said transgene comprises nucleic acid sequence coding for thymidine kinase enzyme.

6. The method of claim 1, wherein said cancer comprises glioma.

7. The method of claim 1, further comprising administering to said human patient temozolamide.

8. In a method of treating cancer in a human by partial or complete resection of tumor from said human, the improvement comprising:
   a. Inducing an immune response against a viral vector, and then
   b. Administering to said human said viral vector.

9. The method of claim 8, wherein said administering to said human said viral vector comprises administering to the cavity created by said resection of said tumor.

10. The method of claim 8, wherein said viral vector comprises adenovirus.

11. The method of claim 8, wherein said viral vector comprises a transgene.

12. The method of claim 11, wherein said transgene comprises nucleic acid sequence coding for thymidine kinase enzyme.

13. The method of claim 8, wherein said cancer comprises glioma.

14. The method of claim 8, further comprising administering to said human patient temozolamide.

15. A method comprising:
   a. diagnosing cancer in a human, and then
   b. in any sequence:
      performing a partial or complete resection of tumor from said human, and
      determining the level of immunity against a viral vector, and confirming said human has a measurable level of immunity against said vector;
   and then
   c. Administering to said human said viral vector.

16. The method of claim 15, wherein said administering to said human said viral vector comprises administering to the cavity created by said resection of said tumor.

17. The method of claim 15, wherein said viral vector comprises adenovirus.

18. The method of claim 15, wherein said viral vector comprises a transgene.

19. The method of claim 18, wherein said transgene comprises nucleic acid sequence coding for thymidine kinase enzyme.

20. The method of claim 15, wherein said cancer comprises glioma.

21. The method of claim 15, further comprising administering to said human patient temozolamide.

22. A method of treating cancer in a human comprising:
   a. diagnosing cancer in said human,
   b. in any sequence:
      performing a partial or complete resection of tumor from said human, and
      Inducing an immune response against a viral vector, and then administering to said human said viral vector.

23. The method of claim 22, wherein said administering to said human said viral vector comprises administering to the cavity created by said resection of said tumor.

24. The method of claim 22, wherein said viral vector comprises adenovirus.

25. The method of claim 22, wherein said viral vector comprises a transgene.

26. The method of claim 25, wherein said transgene comprises nucleic acid sequence coding for thymidine kinase enzyme.

27. The method of claim 22, wherein said cancer comprises glioma.

28. The method of claim 22, further comprising administering to said human patient temozolamide.

\* \* \* \* \*